United States Patent [19]

Denzinger et al.

[11] 4,345,049

[45] Aug. 17, 1982

[54] PREPARATION OF POLYVINYLPYRROLIDONE-IODINE

[75] Inventors: Walter Denzinger, Speyer; Ferdinand Straub, Hockenheim; Heinrich Hartmann, Limburgerhof, all of Fed. Rep. of Germany

[73] Assignee: BASF Aktiengesellschaft, Fed. Rep. of Germany

[21] Appl. No.: 193,462

[22] Filed: Oct. 3, 1980

[30] Foreign Application Priority Data

Oct. 12, 1979 [DE] Fed. Rep. of Germany ....... 2941387

[51] Int. Cl.$^3$ ................................................ C08F 8/04
[52] U.S. Cl. .................................... 525/339; 525/356; 525/326.9; 525/338
[58] Field of Search ................. 525/338, 339, 336, 362

[56] References Cited

U.S. PATENT DOCUMENTS

| | | | |
|---|---|---|---|
| 2,706,701 | 4/1955 | Beller et al. | 167/70 |
| 2,900,305 | 4/1959 | Siggia | 167/70 |
| 2,914,516 | 11/1959 | Siggia et al. | 528/483 |
| 3,028,300 | 4/1962 | Cantor et al. | 167/17 |
| 3,686,366 | 8/1972 | Winkler | 525/338 |
| 3,898,326 | 8/1975 | Cantor et al. | 424/80 |
| 4,027,083 | 5/1977 | Herrle et al. | 525/336 |
| 4,137,383 | 1/1979 | Sagone et al. | 525/338 |
| 4,200,710 | 4/1980 | Denzinger et al. | 525/356 |

FOREIGN PATENT DOCUMENTS 1037075 8/1958 Fed. Rep. of Germany .
2523618 12/1976 Fed. Rep. of Germany .

*Primary Examiner*—William F. Hamrock
*Attorney, Agent, or Firm*—Keil & Witherspoon

[57] ABSTRACT

A process for the preparation of polyvinylpyrrolidone-iodine, wherein a polyvinylpyrrolidone which has been subjected to hydrogenation is reacted with iodine in a conventional manner. The novel process is particularly suitable for use with low molecular weight polyvinylpyrrolidone, having a K value of from 10 to 20.

9 Claims, No Drawings

PREPARATION OF POLYVINYLPYRROLIDONE-IODINE

The present invention relates to a process for the preparation of the reaction product of polyvinylpyrrolidone (PVP) and elementary iodine, which product is in general referred to as polyvinylpyrrolidone-iodine or, for brevity, PVP-iodine, and which is increasingly finding use by virtue of its germicidal, bactericidal, fungicidal and disinfectant properties.

PVP-iodine is generally marketed as a brown powder which contains about 11% of available iodine, ie. active iodine which is titratable with sodium thiosulfate, and in addition contains about 5.5% of iodine in the form of the iodide. With an iodine-iodide ratio of 2:1, the bonding of the iodine in the PVP-iodine complex is sufficiently strong that the odor of iodine is no longer perceptible and a moist potassium iodide starch paper introduced into the gas space above the PVP-iodine does not develop a color. For practical use, it is necessary that in its formulations, in particular in aqueous solution, the PVP-iodine should lose very little available iodine on storage, ie. that it should be very stable.

A great variety of methods of preparation of a very stable PVP-iodine have been described. For example, according to German Pat. No. 1,037,075 PVP-iodine in powder form is subjected to a lengthy heat after-treatment at 90°–100° C., whilst U.S. Pat. No. 2,900,305 discloses that to prepare a stable PVP-iodine a PVP having a defined moisture content should be used. U.S. Pat. No. 2,826,532 proposes sodium bicarbonate, and U.S. Pat. No. 3,028,300 an iodide, in the form of hydrogen iodide or an alkali metal iodide, as an additive German Published Application DAS No. 2,439,197 states that polyvinylpyrrolidone obtained by polymerization in an anhydrous organic solvent is particularly suitable for the preparation of a stable PVP-iodine. A further improvement with respect to iodine loss of the PVP-iodine complex is achieved by treating the polyvinylpyrrolidone, prepared in an organic solvent, with steam, as disclosed in German Laid-Open Application DOS No. 2,523,618.

Nevertheless, the stability of the commercial products is not always adequate, especially if the PVP used is to be of relatively low molecular weight. PVP-iodine is being used increasingly for disinfecting large wounds and body cavities, and if commercial PVP-iodine, based on a relatively high molecular weight PVP, is used for this purpose it may lead to accumulation of PVP in the body. It has been found that the iodophores prepared by the prior art processes, for example of German Pat. No. 1,037,075 or U.S. Pat. Nos. 2,900,305, 2,826,532, 3,028,300 and 3,898,326, based on a low molecular weight PVP, exhibit greater iodine loss, if the PVP is prepared by polymerization in aqueous solution, using a prior art method. It is true that the PVP-iodine prepared by the methods of German Published Application DAS No. 2,439,197 or German Laid-Open Application DOS No. 2,523,618 loses less iodine, but the preparation of the PVP by polymerization in an organic solvent, and the subsequent steam treatment, are rather troublesome and entail additional costs, since the solvent used for the polymerization is very difficult to purify for re-use.

It is an object of the present invention to provide an economical process for the preparation of a PVP-iodine which has an iodine:iodide ratio of not less than 2:1 and which is stable, in particular in aqueous solution. The PVP-iodine must of course also conform to the requirements of the pharmacopeias, such as United States Pharmacopeia XIX, and, for example, according to Defence Medical Purchase Description (No. 4, 1972) the iodine loss of an aqueous PVP-iodine solution containing 1% of available iodine should, after 14 days' storage at 52° C., not exceed 12%.

We have found that this object is achieved, according to the invention, by providing a process for the preparation of a stable polyvinylpyrrolidone-iodine, wherein a polyvinylpyrrolidone which has been subjected to hydrogenation is reacted with iodine in a conventional manner.

The invention in particular relates to the preparation of a stable PVP-iodine based on a relatively low molecular weight PVP, which has a K value of from 10 to 20 and, by virtue of this low value, is, after use, completely eliminated by the human body.

A suitable method of preparation is to mix the solid polyvinylpyrrolidone powder with a fine iodine powder, for example in a twin-cone mixer or tumbler mixer, at room temperature or slightly elevated temperatures of up to 50° C. Advantageously, this is followed by heating the product for from 5 to 20 hours at from 70° to 100° C.

The amount of iodine used is as a rule from 5 to 25%, preferably from 10 to 20%, based on the total weight of PVP-iodine.

If appropriate, from 5 to 20%, based on total weight, of an iodide, especially potassium iodide, sodium iodide or ammonium iodide, may be added when preparing the PVP-iodine.

At times it is advantageous, for the purpose of accelerating the formation of the iodide, to add a reducing agent to the mixture of polyvinylpyrrolidone and iodine, particularly suitable reducing agents being formic acid and oxalic acid.

It is also possible to prepare stable aqueous PVP-iodine solutions direct from the polyvinylpyrrolidone to be used according to the invention. This may be done by mixing the polyvinylpyrrolidone, iodine and iodide in water to form 20 to 70 percent strength by weight aqueous solutions at room temperature, using an iodine:iodide ratio of not less than 2:1. If desired, the solid product can subsequently be isolated from the PVP-iodine solution by a drying process, for example by spray-drying or spray granulation.

The starting material for the preparation of the novel polyvinylpyrrolidone-iodine can be a polyvinylpyrrolidone prepared by any of a great variety of methods, for example solution polymerization in water or in an organic solvent, or precipitation polymerization in an organic solvent. For economic reasons it is particularly advantageous that a polyvinylpyrrolidone which has been polymerized in water and which has known disadvantages when converted to an iodine complex by conventional methods can be used to prepare a stable PVP-iodine.

The polyvinylpyrrolidone used has a K value of from 10 to 50, but a K value of from 10 to 20 is very particularly preferred.

The hydrogenation of the polyvinylpyrrolidone is carried out by conventional known methods. For example, it may be effected by means of hydrogen in the presence of a hydrogenation catalyst, or by treatment with a complex hydride. Advantageously, the hydrogenation is carried out by means of hydrogen in a 5–50 percent strength by weight aqueous solution of the PVP, at from 20° to 100° C., preferably from 50° to 80° C., under a hydrogen pressure of from 50 to 500 bar, preferably from 200 to 300 bar, for from 1 to 24 hours, as described, for example, in U.S. Pat. No. 2,914,516. Examples of suitable catalysts are the conventional platinum and palladium catalysts, and Raney nickel.

A particularly preferred embodiment of the hydrogenation process is to treat the polyvinylpyrrolidone with a complex hydride, in an amount of from 0.1 to 10%, preferably from 0.5 to 5%, based on the weight of PVP. The hydrides used are particularly the water-soluble hydrides, eg. sodium boranate and lithium boranate, but the reaction can also be carried out with others, eg. $NaBH(OCH_3)_3$, $NaAlH_4$, $LiAlH_4$, $NaAlH_2(OCH_2OCH_3)_2$ and $LiAlH[OC(CH_3)_3]$. The highly reactive complex hydrides are employed in sufficiently low amounts that the lactam group of the polyvinylpyrrolidone is not attacked. The preferred compounds are sodium borohydride, lithium borohydride and lithium aluminum hydride.

The reaction with the complex hydride is preferably carried out in water, and this is feasible in the case of lithium boranate and sodium boranate. In the case of the other complex hydrides, it is advantageous to use a solvent, such as a lower alcohol, eg. methanol, ethanol, isopropanol, n-propanol, n-butanol or tert.-butanol, an ether, eg. dioxane or tetrahydrofuran, or an aromatic, eg. benzene, toluene or xylene. The reaction is carried out at from 1° to 150° C., preferably from 15° to 80° C., the temperature depending on the boiling point of the solvent. If the reaction is carried out in an aqueous or alcoholic solvent, the pH is in general brought to about 7 before the reaction. The reaction time varies from 0.5 to 24, preferably from 2 to 8, hours.

It is known that the oxidative action of the peroxide used for the polymerization can produce carboxyl groups in the polyvinylpyrrolidone. In this special case, it can be advantageous to esterify such groups by a conventional method, for example with diazomethane, prior to the reaction with the hydride.

It has proved very useful to purify the polymer solution, after the reaction with the complex hydride, by a passage over an ion exchanger. Examples of suitable products are ion exchangers based on polystyrene and possessing sulfonic acid groups, carboxyl groups or quaternary ammonium groups, for example the products available under the tradenames ®AMBERLITE (Rohm & Haas Comp.) and ®LEWATIT (Bayer AG), or based on acidic or basic silicates.

The Examples which follow illustrate the invention. Parts are by weight. The K values are determined by the method of H. Fikentscher, Cellulose-Chemie, 13 (1932), 58–64 and 71–74, in 5% strength aqueous solution at 20° C.; $K = k \cdot 10^3$. The iodine loss is determined by storing an aqueous PVP-iodine solution, containing 1% of available iodine, for 15 hours at 80° C. The relatively high temperature of 80° C. has the advantage that it obviates the more involved 14 days' storage at 52° C. and yet gives comparable values. The CO number was measured by DGF Standard Method C-V18 (53). The Lewatit S 100 used is a standard cation exchanger, whilst the Lewatit M 500 is a standard anion exchanger.

EXAMPLE 1

(1a) 750 parts of vinylpyrrolidone are dissolved in 250 parts of water, 0.5 part of an 0.01% strength copper-II chloride solution and 30 parts of a 30% strength hydrogen peroxide solution are added and the polymerization is carried out for 6 hours at 70° C. at a pH of 7.6. The polymer solution is then freeze-dried. The PVP obtained has a K value of 17, a CO number [DGF Standard Method C-V18 (53)] of 23 and a water content of 2.6%.

(1b) 100 g of PVP from Example 1a are dissolved in 100 ml of water, the pH is brought to 7 with aqueous ammonia, 5 g of Raney nickel are added and the hydrogenation is carried out for 8 hours at 50° C. in a hydrogenation autoclave under a hydrogen pressure of 200 bar. The Raney nickel is filtered off and the PVP is freeze-dried. It has a CO number of 7 and a water content of 2.9%.

(1c) 100 parts of the PVP from Example 1a are dissolved in 160 parts of water and the pH is brought to 7.5 with 10 parts by volume of 25% strength aqueous ammonia solution. 2 parts of sodium boranate are added, a little at a time, to the solution. The mixture is stirred for about 1 hour at room temperature and is then left to stand overnight, after which it is purified successively with 2,000 parts of Lewatit S 100 and 2,000 parts of Lewatit M 500. The solution is then freeze-dried. The CO number is 5 and the water content 2.3%.

(1d) 100 parts of PVP from Example 1a are dissolved in 250 parts by volume of ethanol and diazomethane is added, to esterify any carboxyl groups present, until a yellow color persists. The mixture is left to stand for 2 days at room temperature, the ethanol is distilled off in steam, and the aqueous solution is spray-dried. 140 parts of PVP are obtained. 50 parts thereof are dissolved in 225 parts of dioxane and 0.5 part of sodium boranate and 1.15 parts of lithium bromide (so that the actual reducing agent is lithium boranate) are added. The mixture turns cloudy. It is left to stand overnight, after which 80 parts of water are added and the dioxane is distilled off in steam. The aqueous solution is successively purified over 2,000 parts of Lewatit S 100 and 2,000 parts of Lewatit M 500, and is spray-dried. The CO number is 2 and the water content 3%.

EXAMPLE 2

(2a) 500 parts of vinylpyrrolidone are dissolved in 400 parts of water, 1 part of an 0.01% strength copper chloride solution and 125 parts of a 30% strength hydrogen peroxide solution are added and the polymerization is carried out for 7 hours at 70° C. To maintain a pH of 7.5, 27 parts by volume of 25% strength ammonia are added in the course of the polymerization. The solid PVP is isolated by freeze-drying. The CO number is 34 and the water content 2.3%.

(2b) The polymerization is carried out as described in 2a. 25 parts of sodium boranate are then added, a little at a time, to the polymer solution at room temperature, and the mixture is stirred for 5 hours. It is then left to stand overnight, after which the solution is purified by treating it with 2,000 parts by volume of Lewatit S 100 and 2,000 parts by volume of Lewatit M 500 ion exchangers. The PVP is isolated by freeze-drying. The polymer has a K value of 14, a CO number of 4.3 and a water content of 2.6%.

EXAMPLE 3

(3a) 500 parts of vinylpyrrolidone are mixed with 214 parts of isopropanol in a glass flask equipped with a stirrer and reflux condenser, and after addition of 5 parts of tert.-butyl hydroperoxide the mixture is heated to the boiling point, namely 96° C. When this has been reached, 0.5 ppm, based on weight of vinylpyrrolidone, of copper acetylacetonate is added in the form of a very dilute solution in 10 parts of isopropanol, and the batch is heated until the residual vinylpyrrolidone content is <0.5%. The solution is then brought to a PVP content of 30% by adding water, and is steam-stripped until the temperature at which material passes over has reached 98° C.; at this stage 180%, based on PVP, of distillate has been produced. Half of the stripped solution is now spray-dried. The solid product obtained has a K value of 30.5, a CO number of 2.5 and a water content of 2.1%.

(3b) The other half of the polymer solution prepared in Example 3a is brought to a pH of 7.5 with 10 parts by volume of ammonia and 2.5 parts of sodium boranate are added, a little at a time. The mixture is then stirred for about 1 hour at room temperature. Thereafter it is left to stand overnight, and is then purified successively over 1,000 parts of Lewatit S 100 and 1,000 parts of Lewatit M 500, and spray-dried. The polymer obtained has a CO number of <1 and a water content of 3.6%.

EXAMPLE 4

(4a) 225 parts of heptane, 111 parts of vinylpyrrolidone and 1.4 parts of poly(vinyl ethyl ether), of K value 50, as a dispersant are introduced into a stirred glass flask; the batch is flushed with a gentle stream of nitrogen for 15 minutes and then heated to 70° C., 0.6 part of azodiisobutyronitrile is added and heating is continued for 6 hours at 70°–75° C. The polymer precipitates as a fine grit which is filtered off when the mixture has cooled, and is dried under reduced pressure at 50° C. The K value of the polymer is 49 and the CO number is 2.0.

(4b) The polymerization is carried out as described in 4a and the dried polymer is redissolved in 400 parts of distilled water. 2 g of sodium boranate are then added and the mixture is stirred overnight. Thereafter the solution is treated successively with 250 parts by volume of Lewatit S 100 and 250 parts by volume of Lewatit M 500. After freeze-drying, the polymer has a CO number of 1.0 and a water content of 1.6%.

PREPARATION OF PVP-IODINE FROM THE POLYVINYLPYRROLIDONES OBTAINED IN EXAMPLES 1 TO 4

83 parts of polyvinylpyrrolidone are mixed with 17 parts of finely milled iodine for 5 hours in a tumbler mixer, and the mixture is then heated to 90° C. and kept at this temperature for 20 hours. Thereafter the iodine loss is determined.

TABLE 1

| Example No. | Polyvinylpyrrolidone | | | PVP—iodine |
|---|---|---|---|---|
| | K value | CO number | $H_2O$ content [%] | Iodine loss [%] |
| 1a | 17 | 23 | 2.6 | 70 |
| b | 17 | 7 | 2.9 | 35 |
| c | 17 | 5 | 2.3 | 14 |
| d | 17 | 2 | 3.0 | 8 |
| 2a | 14 | 34 | 2.3 | >90 |
| b | 14 | 4.3 | 2.6 | 31.5 |
| 3a | 30.5 | 2.5 | 2.1 | 7.5 |
| b | 30.5 | <1 | 3.6 | 1.8 |
| 4a | 49 | 2.0 | 0 | 14.3 |
| b | 49 | 1.0 | 3.7 | 4.8 |

The Table shows that the PVP-iodine prepared from untreated PVP in each case shows the highest iodine loss, whilst the PVP treated according to the invention, with or without subsequent purification, shows an iodine loss which is lower by a factor of from about 3 to 9.

We claim:

1. A process for the preparation of polyvinylpyrrolidone-iodine which comprises subjecting a polyvinylpyrrolidone having a K value of from 10 to 50 to a hydrogenation treatment and thereafter reacting the resultant polyvinylpyrrolidone with iodine.

2. The process of claim 1, wherein the hydrogenation of the polyvinylpyrrolidone is carried out in aqueous solution, using hydrogen in the presence of a hydrogenation catalyst.

3. The process of claim 1, wherein the hydrogenation of the polyvinylpyrrolidone is carried out using a complex hydride.

4. The process of claim 1, wherein a polyvinylpyrrolidone having a K value of from 10 to 20 is used.

5. The process of claim 4 or claim 1 wherein the polyvinylpyrrolidone is hydrogenated under a hydrogen pressure of from 50 to 500 bar, at a temperature of from 20° to 100° C. for from 1 to 24 hours.

6. The process of claim 5 wherein polyvinylpyrrolidone is hydrogenated under a hydrogen pressure of from 200 to 300 bar, at a temperature of from 70° to 100° C. for from 5 to 20 hours.

7. The process of claim 4 or claim 1, wherein the polyvinylpyrrolidone is hydrogenated by treating the polyvinylpyrrolidone with from 0.1 to 10% by weight of a complex hydride based on the weight of polyvinylpyrrolidone.

8. The process of claim 7, wherein the complex hydride is selected from the group consisting of sodium boranate, lithium boranate, $NaBH(OCH_3)_3$, $NaAlH_4$, $NaAlH_2(OCH_2OCH_3)_2$ and $LiAlH[OC(CH_3)_3]$.

9. The process of claim 3, wherein the hydrogenated polyvinylpyrrolidone is treated with an anion exchanger and a cation exchanger.

* * * * *